Figure 1:
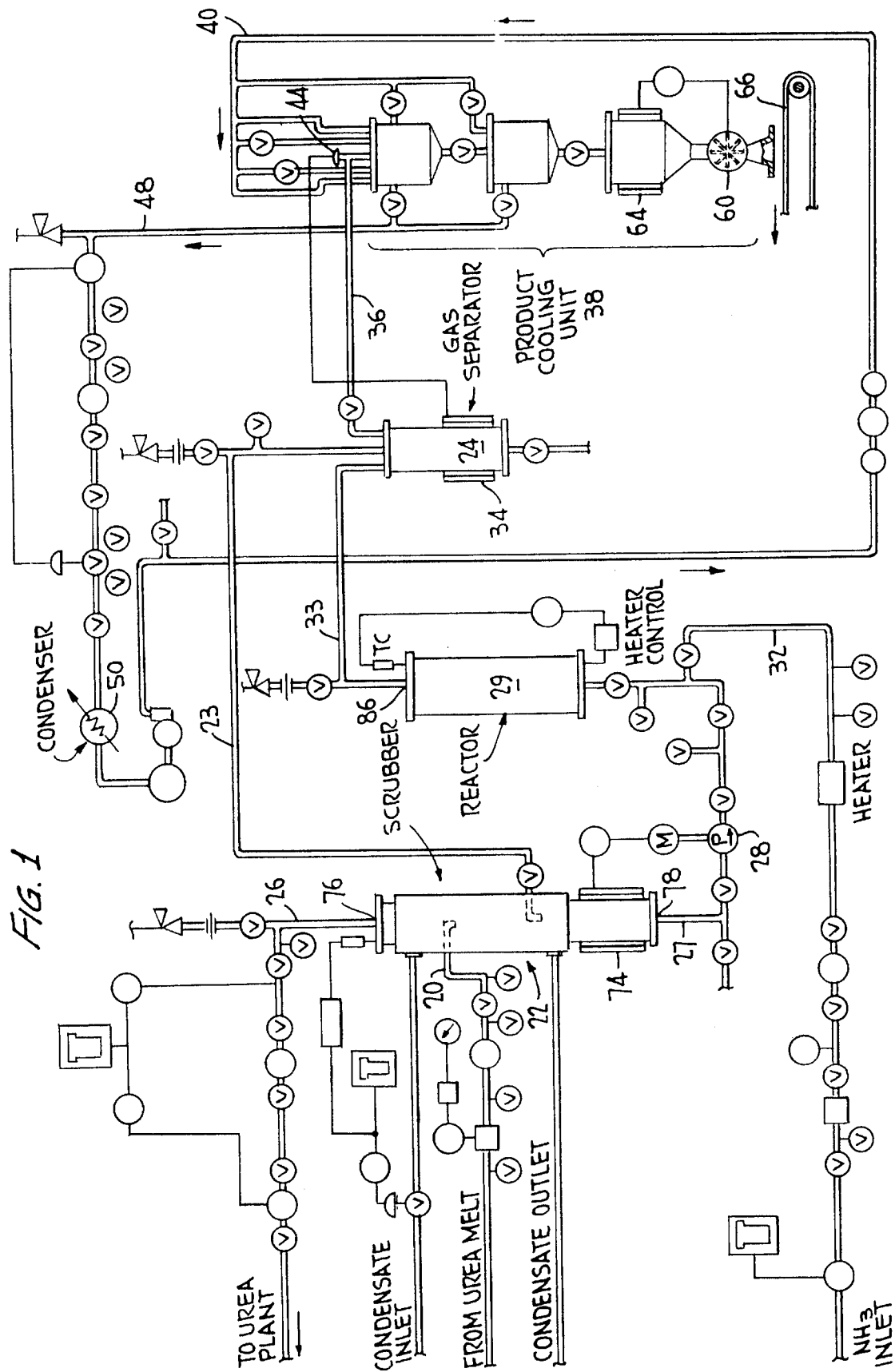

United States Patent [19]
Best et al.

[11] Patent Number: 5,514,796
[45] Date of Patent: May 7, 1996

[54] MELAMINE OF IMPROVED PURITY PRODUCED BY HIGH-PRESSURE, NON-CATALYTIC PROCESS

[75] Inventors: David Best, Prairieville; Amit Gupta, Baton Rouge, both of La.

[73] Assignee: Melamine Chemicals, Inc., Donaldsonville, La.

[21] Appl. No.: 478,088

[22] Filed: Jun. 7, 1995

[51] Int. Cl.⁶ .................................................. C07D 251/60
[52] U.S. Cl. .................................................. 544/201
[58] Field of Search ...................................... 544/201

[56] References Cited

U.S. PATENT DOCUMENTS 4,565,867  1/1986  Thomas ..................................... 544/201

Primary Examiner—John M. Ford
Attorney, Agent, or Firm—Breiner & Breiner

[57] ABSTRACT

A high-pressure, non-catalytic process for producing melamine from urea wherein the melamine is recovered directly as a dry powder without washing or recrystallization is described. In the process, liquid melamine is fed to a cooling unit where it is quenched with a liquid medium, preferably liquid ammonia. By increasing the pressure within the cooling unit to a pressure in excess of 600 psi and preferably to 1200 to 1400 psi provides melamine having a purity in excess of 99%.

9 Claims, 2 Drawing Sheets

MELAMINE OF IMPROVED PURITY PRODUCED BY HIGH-PRESSURE, NON-CATALYTIC PROCESS

FIELD OF INVENTION

The present invention is directed to a high-pressure, non-catalytic, non-aqueous process for producing melamine from urea wherein the melamine is recovered directly as a dry powder without washing or recrystallization. More particularly, the present invention is directed to an improvement wherein the melamine as provided has consistently a purity of 99.0% or above.

BACKGROUND OF INVENTION

Melamine is commercially produced by heating urea to provide melamine and ammonia and carbon dioxide as by products. The basic reaction is

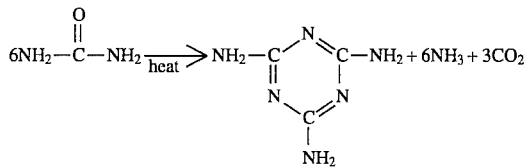

The commercial processes are either high-pressure, non-catalytic or low-pressure and catalytic using a catalyst such as alumina. Conventionally, in low-pressure, catalytic processes the melamine is recovered in an impure form and, subsequently, recrystallized using a chemical treatment to provide melamine which is essentially 100% pure. Similar, chemical treatment and recrystallization steps were used in producing pure melamine with the high-pressure, non-catalytic process.

U.S. Pat. No. 4,565,867 issued Jan. 21, 1986 and assigned to the assignee of the present application, describes a high-pressure process wherein the melamine is recovered at a relatively high purity and used in that form without a crystallization step. The process is highly efficient and provides a low cost melamine. In carrying out the process, urea melt is fed into a scrubber unit at from about 1500 to 2500 psi pressure, preferably from about 1700 to 2200 psi, and at a temperature above the melting point of urea. In the scrubber unit, the liquid urea contacts reaction offgases principally composed of $CO_2$ and $NH_3$ and containing melamine. The urea, in molten condition, scrubs the melamine from the offgas. In the scrubbing process, the offgases are cooled from about the temperature of the reactor, i.e., from about 670° to 800° F. to from about 350° to 450° F. The temperature and pressure are interrelated. If the pressure is at the low end of the range, i.e., 1500 to 1700 psi, the minimum temperature of the scrubber will vary from about 350° to 360° F.; whereas if the scrubber is at the high end of the pressure range, i.e., 2000 to 2200 psi, the minimum temperature can be increased to about 360° to 380° F. Below the above minimum temperatures ammonia and $CO_2$ condense in the bottom of the scrubber and may form carbamate which can be detrimental. As a rule of thumb, the higher the pressure the higher the required minimum temperature. Above about 500° F. the urea may react to form intermediate products. These intermediate products can be detrimental.

A gas separator is provided in the system wherein liquid melamine is separated from offgases, and liquid melamine is collected in the bottom of the separator. The separator is held at a temperature above the melting point of melamine. The gaseous ammonia and carbon dioxide saturated with melamine vapor are removed overhead and fed into the urea scrubber. The liquid melamine is removed from the gas separator on level control and injected into a product cooling unit.

A unique feature of the process described in the '867 patent is the cooling unit wherein liquid melamine recovered from the separator is depressurized and rapidly cooled with a liquid medium which will form a gas at the temperature of the liquid melamine. By utilizing the rapid depressurization and quenching, the liquid melamine is directly converted to a solid powder having a high purity without washing or further purification. As is disclosed in the '876 patent, the liquid quenching agent is a low boiling liquid which gasifies with the gas being readily separated from the solid melamine product. Suitable quenching agents are ammonia, water, or a low boiling alcohol. As further disclosed in the '867 patent, the pressure of the quenching can be atmospheric pressure or a pressure up to about 600 psi. According to the '867 patent, it was preferred to operate at a pressure of about 200 to 400 psi and a temperature of from about 120° to 165° F. In the disclosed process the pressure, as above defined, is the same in the scrubber, reactor, and gas separator. The offgases removed from the gas separator are at the same temperature as the reactor and separator until they reach the scrubber where they are cooled in the process of being scrubbed with the molten urea. The liquid melamine transferred from the gas separator enters the product cooling unit at the same temperature range as the reactor and gas separator.

Although the process of the '867 patent has produced melamine in the range of 96 to 99.5% melamine which contains low levels of melem and melam, the process of the '867 patent in commercial operation has only produced melamine in the range of about 97.5% with the main impurities being melem, melam, urediomelamine and ammeline. Although this product is usable in most melamine markets, it is limited in some because of the impurities. In high pressure melamine technologies other than as described in the '867 patent, the impurities are removed by using a chemical treatment and then a recrystallization process. The impurities are converted to components that can be removed from the product by either filtration or sedimentation or both. This reduces the yield of melamine from urea by removing these impurities and also increases the disposal cost by having to dispose of the filter cake.

There is a need, therefore, to produce a more pure melamine, namely 99+ percent, on a commercial basis without either recrystallizing or having to dispose of the by products.

OBJECTS AND SUMMARY OF THE INVENTION

It is a primary object of the present invention to produce high purity melamine directly from an anhydrous high-pressure melamine synthesis process without the need to dispose of the impurities or to require an expensive recrystallization step.

The aforesaid and other objectives of this invention are accomplished by use of a continuous product cooling unit in conjunction with a high pressure, non-catalytic system, particularly the Melamine Chemicals, Inc. Anhydrous High-Pressure Melamine Synthesis disclosed in the '867 patent, incorporated herein by reference.

Thus, according to the present invention melamine melt, or liquid melamine, is removed from the gas separator and flowed into the product cooling unit. In the product cooling unit the liquid is rapidly cooled and depressurized using a liquid medium that is a vapor at the conditions of the cooling unit, preferably ammonia. Dry melamine powder is formed. The melamine powder is removed from the bottom of the product cooling unit. The product cooling unit is preferably maintained at a temperature below the melt point of melamine and the reaction temperature of urea. The minimum temperature is the vapor temperature equilibrium of the cooling liquid.

The pressure of the cooling unit is the critical feature of the present invention along with the rapid cooling of the melamine. Thus, surprisingly, it has been found that rather than keeping the cooling unit at atmospheric or up to about 600 psi, a pressure of at least 600 psi is essential to prevent the formation of melam, melem, and the other impurities to obtain melamine of 99+ percent purity. The preferred pressure is a pressure from about 1200 to about 1600 psi. It is theorized that the high pressure prevents side reactions and deamination as the rapid quench and cooling occurs, and in this way prevents the formation of any unwanted impurities.

THE DRAWING AND DETAILED DESCRIPTION

Having described the invention in general terms, a detailed description of a preferred embodiment will be described in relation to the drawing. In the drawing, wherein like numbers represent like elements.

Figure 2:
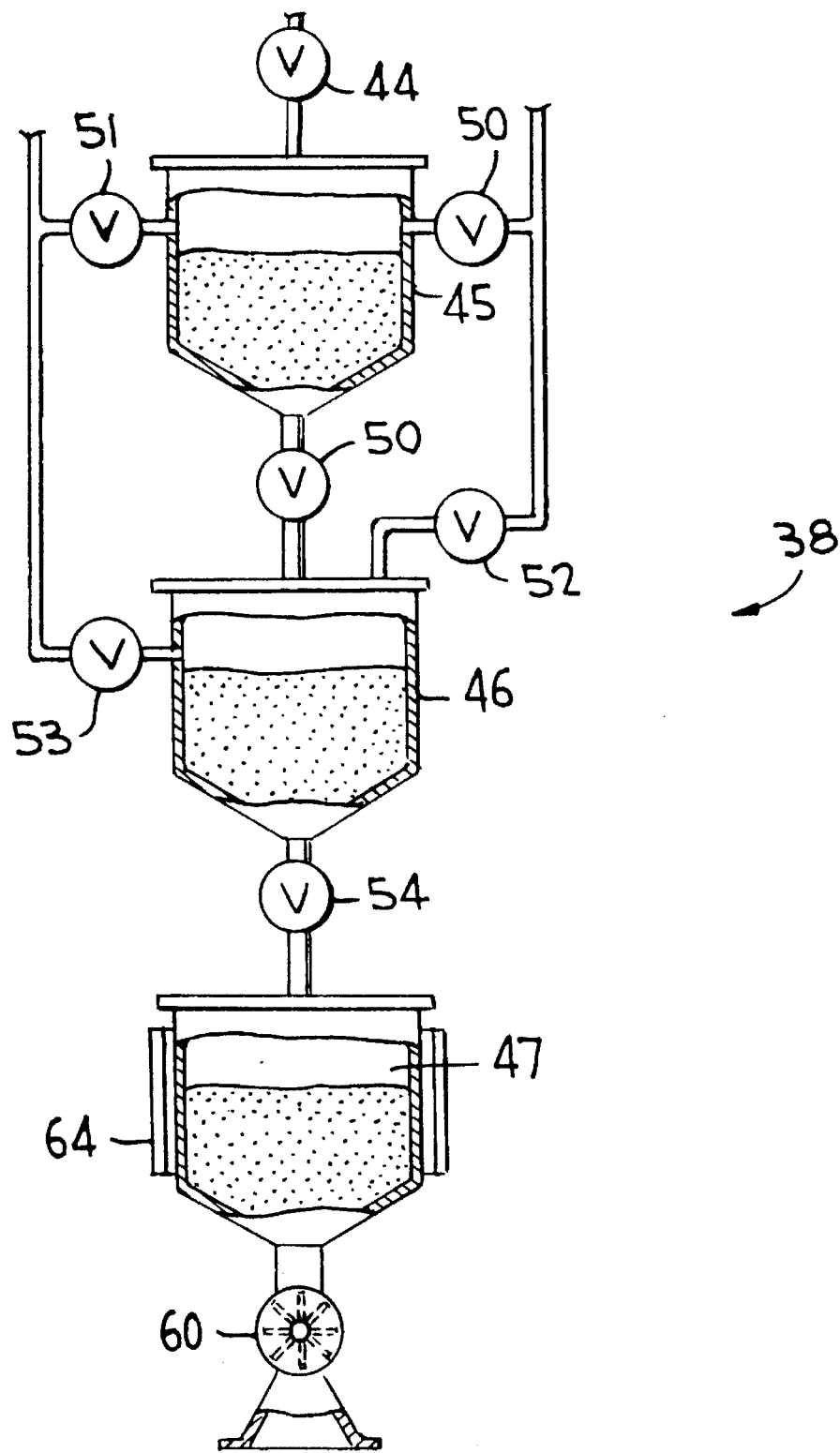

FIG. 1 is a flow diagram of a complete plant-system according to the present invention for the manufacture of melamine product from urea; and FIG. 2 is an elevational view in section of the product cooling unit.

The flow diagram of FIG. 1 diagrammatically illustrates the present invention. Urea is fed through line 20 to scrubber unit 22 at a temperature above the melting point of urea, and preferably at about 280° F.; and at a pressure of from about 1700 to 3500 psi. In the continuous process, scrubber unit 22 is also fed through line 23 with offgases from separator 24. The offgases, consisting primarily of ammonia, carbon dioxide and melamine, will be at a temperature of approximately 700° to 800° F. and at a pressure of from about 1700 to 3500 psi, i.e., the reaction conditions of the reactor and separator unit. The stream composition from the separator unit will be approximately 45 to 65% ammonia, 30 to 50% carbon dioxide, and 3 to 10% melamine. The molten urea will be used to "scrub" the melamine from the offgases, giving off heat energy to preheat the urea and reducing the temperature of the offgases to about 350° to 450° F. The urea containing the melamine will settle at the bottom of the scrubber 22. The purified ammonia and carbon dioxide gases at the reduced temperature is fed through line 26 to a urea plant for utilization in producing urea, or any unit that utilizes the $NH_3/CO_2$ blend or separates it so that the ammonia can be used.

The scrubber bottoms are removed from the bottom of the scrubber and fed through line 27 by means of a pump 28 at a temperature of from about 350° to 450° F., and a pressure of from about 1700 to 3500 psi into reactor 29. Ammonia from a suitable ammonia source is pumped through line 32 into the urea stream from the scrubber. The hot ammonia which is injected into the line carrying the scrubber bottoms acts as a purge to keep the bottom of the reactor from plugging and supplies excess ammonia to react with any deammoniation product which may be present. The reactor will also be maintained at an operating temperature of from about 700° to 800° F., and a pressure of from 1700 to 3500 psi. The reactor, which is resistant to corrosion, i.e., titanium-clad carbon steel; preferably includes means to circulate the reactant within the reactor. The preferred reactor temperature is about 770° F. and the preferred pressure is 2000 psi. The reactor is temperature controlled using conventional heat control systems including thermocouples.

The product of the reactor, comprised primarily of ammonia, carbon dioxide and melamine, is fed to gas separator 24. The reaction product is released into the top of the separator. In the separator the gaseous by-products consisting of ammonia, carbon dioxide and melamine which are fed to the scrubber unit 22 through line 23 are removed from the top of the separator. Liquid melamine is removed from substantially the bottom one-third of the separator controlled by level indicator at a temperature of approximately 700° to 800° F., and a pressure of about 1700 to 3500 psi, and fed through line 36 to the product cooling unit 38.

The product cooling unit comprises three compartments 45, 46 and 47. The liquid melamine from line 36 is let down through valve 44 into compartment 45 with liquid ammonia being simultaneously flushed into compartment 45 through line 40 to quench and rapidly cool the liquid melamine to provide solid melamine. Ammonia is cooled and recirculated from compartment 45 through valve 51. The pressure within compartment 45 after quenching is at approximately 1200 psi and at a temperature of 350° to 450° F. The pressure of compartments 45 and 46 is equalized by feeding ammonia vapor through valve 52 into compartment 46. When the two compartments are at an equal pressure, the solid melamine is let down from compartment 45 into compartment 46 through valve 50. After the solid melamine is in compartment 46 at the pressure of approximately 1200 psi, valve 50 is closed and the pressure within compartment 46 is reduced to atmospheric by releasing ammonia through valve 53 for recirculation. Thereafter, valve 54 is opened and the solid melamine is dropped into compartment 47. The solid melamine product is continuously removed from compartment 47 through a rotary valve 60 controlled by a level control 64. The melamine product is released through rotary valve 60 onto a suitable conveyor 66 for subsequent bagging or the like.

The efficiency of the present process is established from the data set forth in the Table. Thus, in the Table, Sample No. 1 is a process as defined in the '867 patent where the cooling unit is at a pressure of about 600 psi and at a temperature of about 150° F. Sample Nos. 2 through 6 are produced according to the present invention, where the pressure within the cooling unit is in the range of 800 to 1400 psi and at a temperature of about 350° to 450° F. As is apparent, the level of impurities is substantially reduced. This level of reduction of impurities is surprising and is unexpected, providing an enhanced commerical system.

TABLE

| Sample No. | Analysis | | | | | |
| --- | --- | --- | --- | --- | --- | --- |
| | 1 | 2 | 3 | 4 | 5 | 6 |
| Ammelide | 0.0 | 0.0 | 0. | 0.0141 | 0.0 | 0.0 |
| Ammeline | 0.11 | 0.0098 | 0.0225 | 0.0470 | 0.0225 | 0.0183 |
| Melamine | 97.5 | 99.96 | 99.54 | 99.84 | 99.04 | 99.51 |
| Ureido | 0.65 | 0.0 | 0.0 | 0.0 | 0.0 | 0.0 |
| Melem | 0.139 | 0.0132 | 0.417 | 0.3182 | 0.1295 | 0.4507 |
| Melam | 1.92 | 0.0145 | 0.013 | 0.1354 | 0.8009 | 0.0140 |

The present invention is not directed to any specific high temperature process but, preferably, is a high pressure process such as described in the '867 patent. The invention can be utilized, however, with other high-pressure, non-catalyst systems.

As will be apparent to one skilled in the art, various modifications can be made within the scope of the above description. Such modification being within the ability of one skilled in the art form a part of the present invention and are embraced by the appended claims.

It is claimed:

1. A continuous process for producing melamine from urea comprising pyrolyzing urea in a reactor at a pressure at from about 1500 to 3500 psi and at a temperature at from about 670° to 850° F. to produce a reaction product containing liquid melamine, $CO_2$ and $NH_3$; transferring, under pressure, said reaction product as a mixed stream to a separator unit; maintaining said separator unit at substantially the same pressure and temperature as said reactor; separating said reaction product in said separator unit into $CO_2$ and $NH_3$ offgases containing melamine vapors and liquid melamine; simultaneously transferring (a) said $CO_2$ and $NH_3$ offgases containing melamine at a temperature and pressure substantially the same as said temperature and pressure of said separator unit to a scrubber unit and scrubbing said offgases with molten urea to preheat said urea and cool said offgases and remove therefrom said melamine, and thereafter removing $NH_3$ and $CO_2$ gases from said scrubber unit at a temperature of from about 350° to about 450° F. and feeding said preheated molten urea containing said melamine to said reactor, and (b) said liquid melamine to a product cooling unit; and depressurizing and quenching said liquid melamine with a liquid medium which will form a gas at the temperature of said liquid melamine in said product cooling unit, said cooling unit being at a pressure in excess of 600 psi to produce a commercially useful solid melamine product having a purity in excess of 99% without washing or further purification.

2. The process of claim 1 wherein said melamine product has a purity of from about 99.5 to 99.8% melamine, and contains not more than about 1.5% melem and melam.

3. The process of claim 1 wherein said reactor is at a pressure of from 1700 to 3500 psi and at a temperature of from 700° to 850° F., said gas separator being maintained at substantially said pressure and temperature of said reactor, and said scrubber being maintained at substantially the same pressure of said reactor.

4. The process of claim 3 wherein said liquid for quenching said liquid melamine is anhydrous liquid ammonia.

5. The process of claim 4 wherein the product cooling unit is maintained at a pressure of from about 1200 to 1400 psi and at a temperature of from about 350° to 450° F.

6. In a high-pressure, non-catalytic process for producing melamine from urea wherein liquid melamine is produced and quenched to provide solid melamine powder, the improvement wherein the liquid melamine is fed to a cooling unit where it is quenched with a liquid medium which will form a gas at the temperature of said liquid melamine at a pressure in excess of 600 psi to provide melamine having a purity in excess of 99%.

7. The process of claim 6 wherein the pressure is from about 1000 to 1600 psi and the temperature is at about 350° to 450° F.

8. The process of claims 6 or 7 wherein the liquid used for quenching the liquid melamine is anhydrous liquid ammonia.

9. The process of claim 6 wherein the pressure is from about 1000 to 2500 psi and the temperature is at about 350° to 450° F.

* * * * *